(12) United States Patent
Andreyev et al.

(10) Patent No.: US 10,925,554 B2
(45) Date of Patent: Feb. 23, 2021

(54) OUTSIDE-FOV ACTIVITY ESTIMATION USING SURVIEW AND PRIOR PATIENT DATA IN POSITRON EMISSION TOMOGRAPHY

(71) Applicant: KONINKLIJKE PHILIPS N.V., Eindhoven (NL)

(72) Inventors: Andriy Andreyev, Willoughby Hills, OH (US); Manoj Narayanan, Mentor, OH (US); Bin Zhang, Cleveland, OH (US); Zhiqiang Hu, Twinsburg, OH (US); Yu-Lung Hsieh, Aurora, OH (US); Xiyun Song, Cupertino, CA (US); Jinghan Ye, Cupertino, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 855 days.

(21) Appl. No.: 15/533,749

(22) PCT Filed: Dec. 3, 2015

(86) PCT No.: PCT/IB2015/059311
§ 371 (c)(1),
(2) Date: Jun. 7, 2017

(87) PCT Pub. No.: WO2016/092428
PCT Pub. Date: Jun. 16, 2016

(65) Prior Publication Data
US 2017/0319154 A1    Nov. 9, 2017

Related U.S. Application Data

(60) Provisional application No. 62/089,879, filed on Dec. 10, 2014.

(51) Int. Cl.
*A61B 6/00* (2006.01)
*A61B 6/03* (2006.01)
(Continued)

(52) U.S. Cl.
CPC ............ *A61B 6/037* (2013.01); *A61B 5/0077* (2013.01); *A61B 5/055* (2013.01); *A61B 6/032* (2013.01);
(Continued)

(58) Field of Classification Search
CPC ..................................................... A61B 6/037
See application file for complete search history.

(56) References Cited

U.S. PATENT DOCUMENTS 7,312,455 B2   12/2007   Manjewshwar
8,415,630 B2    4/2013   Ross
(Continued)

FOREIGN PATENT DOCUMENTS

WO    2006/049523    5/2006
WO    2010/095062    8/2010

*Primary Examiner* — Joseph M Santos Rodriguez

(57) ABSTRACT

A radioemission scanner (12) is operated to acquire tomographic radioemission data of a radiopharmaceutical in a subject in an imaging field of view (FOV). An imaging system is operated to acquire extension imaging data of the subject in an extended FOV disposed outside of and adjacent the imaging FOV along an axial direction (18). A distribution of the radiopharmaceutical in the subject in the extended FOV is estimated based on the extension imaging data, and further based on a database (32) of reference subjects. The tomographic radioemission data are reconstructed to generate a reconstructed image (26) of the subject in the imaging FOV. The reconstruction includes correcting the reconstructed image for scatter from the extended FOV into the imaging FOV based on the estimated distribution of the radiopharmaceutical in the subject in the extended FOV.

20 Claims, 4 Drawing Sheets

(51) Int. Cl.
*G06T 11/00* (2006.01)
*G01T 1/16* (2006.01)
*A61B 5/00* (2006.01)
*A61B 5/055* (2006.01)

(52) U.S. Cl.
CPC .......... *A61B 6/4258* (2013.01); *A61B 6/4417* (2013.01); *A61B 6/483* (2013.01); *A61B 6/488* (2013.01); *A61B 6/5205* (2013.01); *A61B 6/5247* (2013.01); *A61B 6/5282* (2013.01); *G01T 1/1603* (2013.01); *G06T 11/005* (2013.01); *G06T 2211/432* (2013.01)

(56) References Cited

U.S. PATENT DOCUMENTS

| | | |
|---|---|---|
| 8,768,432 B2 | 7/2014 | Ladebeck |
| 2008/0317194 A1 | 12/2008 | Gagnon |
| 2010/0116994 A1 | 5/2010 | Wollenweber |
| 2011/0058722 A1* | 3/2011 | Hu .................. G06T 11/006 382/131 |
| 2011/0288407 A1 | 11/2011 | Brinks |
| 2013/0026370 A1 | 1/2013 | Qian |

\* cited by examiner

OUTSIDE-FOV ACTIVITY ESTIMATION USING SURVEY AND PRIOR PATIENT DATA IN POSITRON EMISSION TOMOGRAPHY

CROSS REFERENCE TO RELATED APPLICATIONS

This application is the U.S. National Phase application under 35 U.S.C. § 371 of International Application No. PCT/I132015/059311, filed Dec. 3, 2015, published as WO 2016/092428 on Jun. 16, 2016, which claims the benefit of U.S. Provisional Patent Application No. 62/089,879 filed Dec. 10, 2014. These applications are hereby incorporated by reference herein.

The following relates generally to imaging in nuclear medicine. One imaging technique in nuclear medicine is positron emission tomography (PET), which images the distribution of injected radiopharmaceutical inside a patient's body, revealing important physiological processes. Its main clinical applications are in the field of oncological, neurologic, and cardiac imaging. Current state-of-the-art PET cameras use the following typical workflow. First, the patient is injected a radiopharmaceutical. In most cases, unless it is a dynamic scan studying the tracer kinetics of the injected radiopharmaceutical, there is a certain wait period for the radiopharmaceutical to achieve a physiological distribution, for example, concentrating in a tissue, organ or tumor of interest. The patient is placed on the table which goes into the PET bore (opening of the PET scanner) where the patient is surrounded by one or more rings of PET detectors that allow the detection of two simultaneous 511 keV gammas, emitted from an annihilating positron of PET radiopharmaceutical. Each detected pair of events defines a straight line-of-response which intersects the emission source based on the physics of the positron-electron annihilation. A large collection of such detected events can be subsequently reconstructed using special software, which results in a creation of diagnostically meaningful three-dimensional (3D) images that reveal the spatiotemporal distributions of the injected radiotracers.

The present application provides a new and improved system and method for use in PET and other nuclear imaging systems.

In accordance with one aspect, a radioemission imaging system including an electronic data processing device programmed to perform an imaging method including: operating a radioemission scanner to acquire tomographic radioemission data of a radiopharmaceutical in a subject in an imaging field of view (FOV); operating an imaging system to acquire extension imaging data of the subject in an extended FOV disposed outside of and adjacent the imaging FOV along an axial direction; estimating a distribution of the radiopharmaceutical in the subject in the extended FOV based on the extension imaging data; and reconstructing the tomographic radioemission data to generate a reconstructed image of the subject in the imaging FOV including correcting the reconstructed image for scatter from the extended FOV into the imaging FOV based on the estimated distribution of the radiopharmaceutical in the subject in the extended FOV. The operating of the imaging system may include operating a transmission computed tomography (CT) scanner or magnetic resonance (MR) scanner to acquire an image of the subject in the extended FOV. Additionally, the estimating the distribution of the radiopharmaceutical in the subject in the extended FOV may be based on (i) the acquired image of the subject in the extended FOV and (ii) a database of distributions of the radiopharmaceutical in other subjects. If the database of distributions of the radiopharmaceutical in other subjects is used, a distribution of the radiopharmaceutical in another subject that most closely matches the acquired two-dimensional radioemission data of the subject in the extended FOV may be selected. Further, if the database of distributions of the radiopharmaceutical in other subjects is used, the estimation may further comprise adjusting the selected distribution of the radiopharmaceutical in another subject based on either the acquired two-dimensional radioemission data of the subject in the extended FOV, or a characteristic of the subject (such as weight, height, etc).

In accordance with another aspect, in a radioemission imaging system as set forth in the immediately preceding paragraph, the radioemission scanner may be operated to acquire a fast whole body radio emission image which has lower counting statistics and resolution than the reconstructed image inside FOV, and the estimating may include estimating the distribution of the radiopharmaceutical in the subject in the extended FOV based on the whole-body radioemission image of the subject. Additionally, the processing may include correcting the reconstructed image inside FOV for the estimated distribution of the radiopharmaceutical in the subject in the extended FOV using single scatter simulation.

In accordance with another aspect, the scanner may be a PET scanner. The scanner may also be any other kind of a scanner, such as a single-photon emission computed tomography (SPECT) scanner or a Compton camera.

In accordance with another aspect, a non-transitory storage medium storing instructions readable and executable by an electronic data processing device to perform an imaging method including: receiving tomographic radioemission data of a radiopharmaceutical in a subject in an imaging field of view (FOV); receiving extension imaging data of the subject in an extended FOV neighboring the imaging FOV; estimating a distribution of the radiopharmaceutical in the subject in the extended FOV based on the extension imaging data; and reconstructing the tomographic radioemission data to generate a reconstructed image of the subject in the imaging FOV. The reconstruction includes correcting the reconstructed image for scatter from the estimated distribution of the radiopharmaceutical in the subject in the extended FOV.

In accordance with another aspect, an imaging method including: acquiring tomographic radioemission data of a radiopharmaceutical in a subject in an imaging field of view (FOV); acquiring extension imaging data of the subject in an extended FOV extending beyond the imaging FOV along an axial direction; estimating a distribution of the radiopharmaceutical in the subject in the extended FOV based on the extension imaging data; and reconstructing the tomographic radioemission data to generate a reconstructed image of the subject in the imaging FOV including correcting the reconstructed image for scatter into the imaging FOV from the estimated distribution of the radiopharmaceutical in the subject in the extended FOV.

One advantage resides in improvement in image quality and quantitation when trying to correct for spurious outside-FOV activity impact in many cases of clinical radioemission scanning. It will be especially useful when the FOV neighbors a region with a very high activity distribution such as the bladder.

The invention may take form in various components and arrangements of components, and in various steps and arrangements of steps. The drawings are only for purposes of illustrating the preferred embodiments and are not to be construed as limiting the invention.

FIG. 1 diagrammatically shows an embodiment of a radioemission imaging system.

Typically, PET scanner acquisition workflow is restricted to a certain region of interest or field-of-view (FOV), and the PET data outside-FOV are not routinely collected in order to save scanning time. However, it is still important to have an estimate of outside-FOV radiopharmaceutical distribution in order to have an accurate estimate for scatter correction methods.

Figure 1:
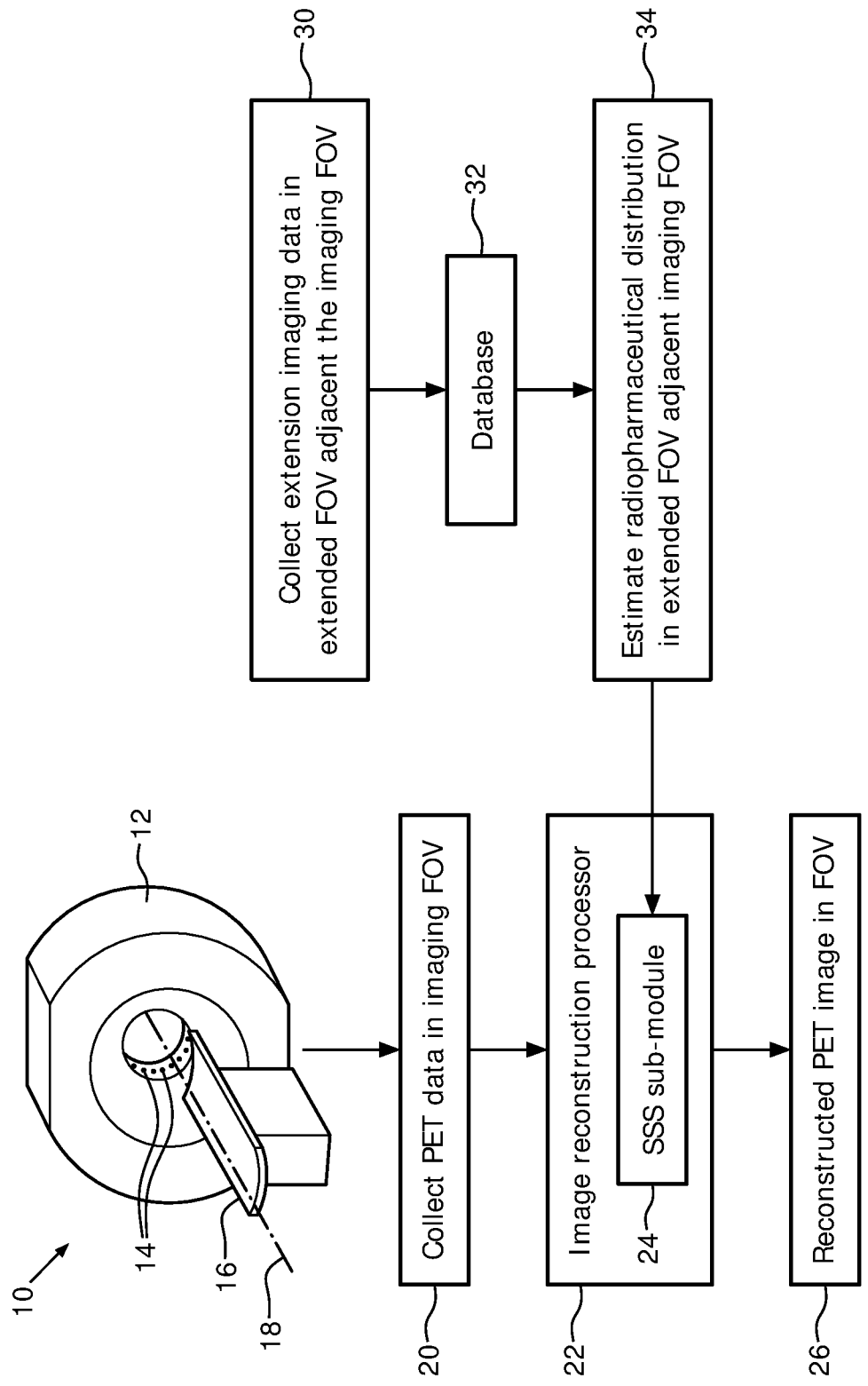

With reference to FIG. 1, an illustrative radioemission imaging system 10 includes a positron emission tomography (PET) scanner 12 with radiation detectors 14. The scanner 12 and radiation detectors 14 are arranged and sized to receive a prone human subject on a table 16 in an examination region that is surrounded by the ring of radiation detectors 14. Although in diagrammatic FIG. 1 the radiation detectors 14 are illustrated, it will be appreciated that in typical commercial PET scanners the radiation detectors are enclosed inside the housing of the PET scanner 12 and hence are not usually externally visible. The PET scanner 12 may be a conventional PET scanner or may incorporate time-of-flight (TOF) capability, in which the positron annihilation event is localized along the line-of-response based on differential detection times of the two 511 keV gamma particles. Some suitable PET scanners include various PET scanners available from Koninklijke Philips N.V. (Eindhoven, the Netherlands).

In PET imaging, a subject is administered a radiopharmaceutical that includes a positron-emitting radioisotope. The radiopharmaceutical may be designed to aggregate in an organ or tissue of interest, such as the brain, lungs, a tumor, or so forth. After administration of the radiopharmaceutical, the subject is loaded into the examination region. As time progresses, the radiopharmaceutical will emit positrons at events through a processes known as positive beta decay. A positron emitted by the radiopharmaceutical will travel for a short distance. As it travels it will lose energy, and as it losses energy, it becomes more likely to interact with an electron. Once the positron interacts with the electron, both the positron and the electron will be annihilated (electron-positron annihilation) and a pair of 511 keV gamma photons (sometimes also called annihilation photons) are produced. The 511 keV gamma photons move in opposite directions and may be detected upon reaching a scintillator in scanner 12. In general, two simultaneously detected (within a defined time window) gamma photon events are assumed with high probability to have been generated by a single positron annihilation event lying along the connecting line of response. In TOF PET, the event is further localized along the line of response based on the time-of-flight information.

While the illustrative radioemission modality is PET, the disclosed techniques for estimating and correcting out-of-field-of-view radioactivity are also applicable to other radioemission imaging modalities, such a single photon emission computed tomography (SPECT, not illustrated). In this technique, only one radiation particle is emitted and the radiation detector includes a collimator to define a line (or small-angle cone) of response.

Figure 2:
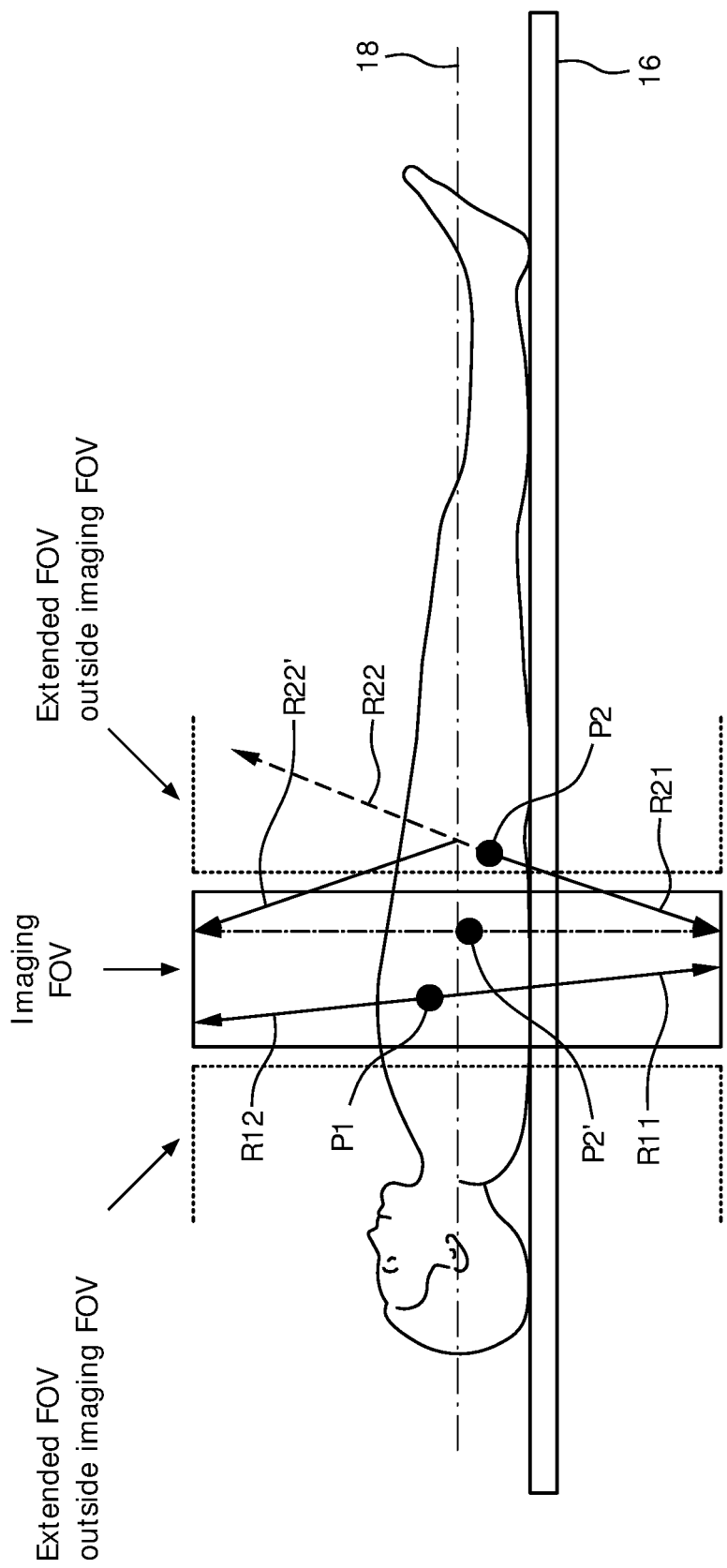
FIG. 2 shows an example of a subject and a FOV area.

With reference to FIGS. 1 and 2, PET scanner 12 collects PET imaging data in a field of view (FOV). Much of the data collected by PET scanner 12 will correspond to events (e.g. at annihilation locations) happening within the FOV. For example, a positron annihilation event P1 occurs inside the FOV and its 511 keV gamma rays R11, R12 are detected to define a line of response. However, some of the data collected by PET scanner 12 will correspond to events happening outside of the FOV that are scattered into the FOV. In the case of a prone patient lying on the table 16, the patient extends along an axial direction 18, so that a non-zero distribution of radiopharmaceutical may be present in an extended FOV disposed outside of and adjacent the imaging FOV along the axial direction 18. An example of this is also shown in FIG. 2: an annihilation event P2 occurring outside the FOV has a first gamma ray R21 that impinges on a PET detector, and a second gamma ray R22 that (in the absence of scatter) would miss the radiation detector ring. In such a case, no PET datum would be generated since only one 511 keV detection event would occur (the one due to the gamma ray R21). However, the illustrative 511 keV gamma ray R22 undergoes a scattering event so that its actual path R22' impinges on a radiation detector. As a consequence, two simultaneous 511 keV detection events are obtained, which define an erroneous line of response which, during image reconstruction, might be misinterpreted as corresponding to a positron annilation event P2'. Such outside-FOV events are principally due to scattering of 511 keV photons during transit, as illustrated.

With returning reference to FIG. 1, in a processing block 20, coincident 511 keV events corresponding to positron annihilation events are identified by time and energy windowing. Most of these are correct events (like the line of response corresponding to the annihilation event P1), but some are erroneous lines of response due to scattering (like the line of response corresponding to the annihilation event P2). The tomographic PET imaging data are reconstructed by a reconstruction processing block 22 into a 3D image of the FOV using a suitable reconstruction process. Some suitable tomographic image reconstruction algorithms include filtered back projection, iterative forward-backward projection algorithms, and Fourier transform reconstruction algorithms.

The tomographic reconstruction algorithm employed by the reconstruction processor 22 typically does not take into account erroneous lines of response due to outside-FOV scattering, such as that due to the event P2. To improve accuracy in reconstructing the data, it is desirable to correct the reconstruction process to account for annihilation events occurring outside the FOV. To this end, in an operation 30 shown in FIG. 1 extension imaging data are acquired of the subject in an extended field of view disposed outside of and adjacent the imaging FOV along the axial direction 18. This may be done, for example, by conducting a computed tomography (CT) scan, a magnetic resonance (MR) scan, or with a photographic camera. In some embodiments, a survey view ("surview") acquired by a CT scanner in preparation for the PET imaging may be used for this purpose. Such imaging systems do not directly image the distribution of the radiopharmaceutical in the subject (rather, they provide anatomical boundaries of the outside FOV regions), but such an image of the subject can be used in combination with an "atlas", i.e. database 32 or other information about how the radiopharmaceutical typically distributes within a subject in order to estimate the distribution in the instant subject undergoing PET imaging. Alternatively, the imaging data from outside the FOV may be collected by operating the PET scanner 12 outside the FOV in a separate rapid scan; for example, the outside FOV information may be collected by an ultrafast whole body PET scan that is of lower counting statistics than the reconstructed image generated for the FOV by the image reconstruction processor 22. Outside FOV data from ultrafast PET scan can be reconstructed to low spatial resolution in order to suppress noise and be effectively used as an estimate of outside FOV activity distribution in scatter correction techniques. Additionally, the techniques of gathering data outside the FOV may be used alone or in combination with each other.

In some embodiments, the operation 30 entails obtaining a surview. In most PET scans, a surview covering a larger axial FOV is acquired for planning purposes, and hence is readily available for use in the scatter correction disclosed herein. The surview is usually created with fixed angle (single projection) axial CT scan, resulting in a 2D transmission image and minimal additional dose to the patient. Alternatively, an optical imaging device (photo-video imaging device) can be used to establish the boundaries of the object. In another variant, a PET surview can be used (10 sec or so per bed position or using quick continuous couch motion) to evaluate the total activity without adding much time and additional dose to the patient.

In embodiments in which the operation 30 does not directly image the radiopharmaceutical distribution (e.g. when CT or MR imaging is used), the distribution is suitably derived using a database (also sometimes referred to as an "atlas") 32 of other subjects. The database suitably contains information of imaged or otherwise quantified distribution of the radiopharmaceutical in other subjects including regions that are outside FOV for a current subject. Database content may be selected for use based on the type of radiopharmaceutical administered to the subject. Database content may further be selected based on one or more characteristics of the subject such as gender, age, height and body-mass-index. The selected database content is used to estimate the radiopharmaceutical distribution outside the FOV in an operation 34.

With continuing reference to FIG. 1, the reconstructing of the tomographic PET data to generate the reconstructed PET image of the subject in the imaging FOV includes correcting the reconstructed image for the estimated distribution of the radiopharmaceutical in the subject in the extended FOV. In the illustrative embodiment, this correction is performed by a sub-module 24 using single scatter simulation (SSS), although more complex techniques (e.g. accounting for both single and double scatter events) are also contemplated. SSS estimates scatter correction factors along lines of responses by summing scatter probabilities provided by a transmission image, anatomical map (e.g. identifying bones or other likely scattering structures), or so forth.

Figure 3A:
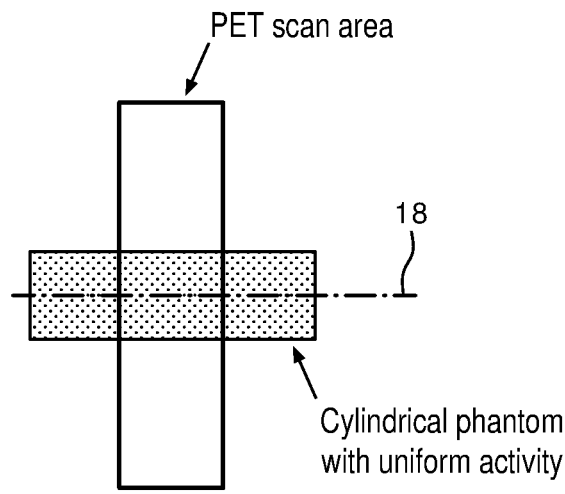
FIG. 3A shows an example representation of a PET scan area and a cylindrical phantom with uniform activity.
Figure 3B:
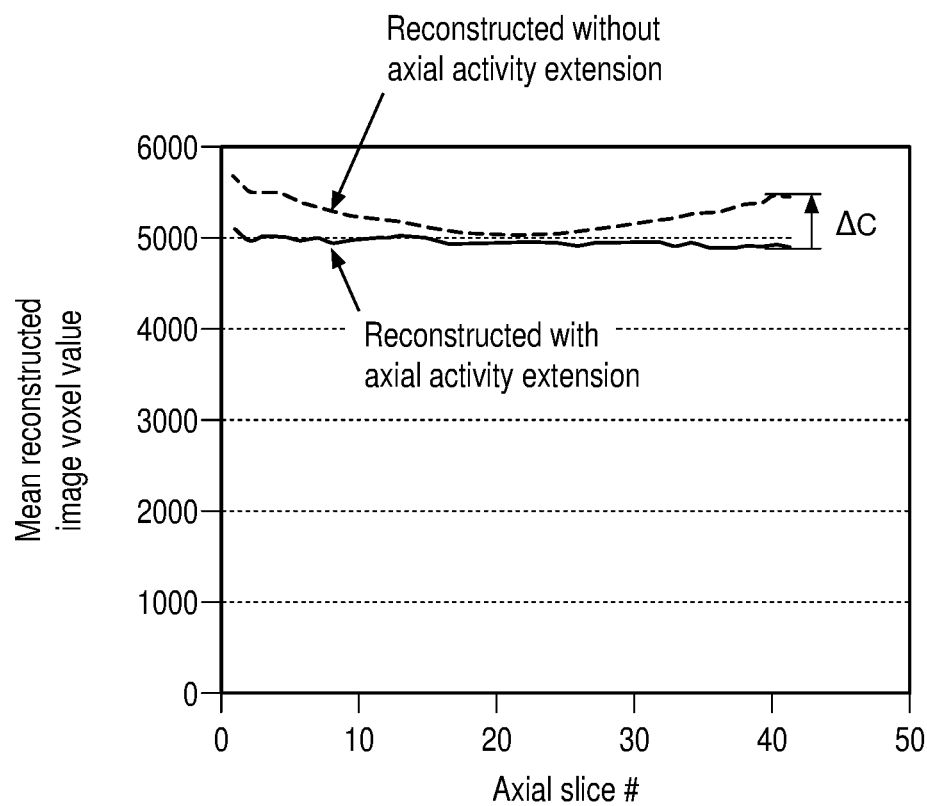
FIG. 3B shows example mean voxel values in a reconstructed image over the uniform activity shown in FIG. 3A.

With reference to FIGS. 3A and 3B, the impact of the outside FOV scatter correction is illustrated. In this experiment, as diagrammatically shown in FIG. 3A, a cylindrical phantom was filled with uniform radioactivity, with the cylindrical phantom extending ~7 cm outside the FOV (PET scan area) on both ends. FIG. 3B shows mean reconstructed image voxel values along the axial direction (i.e. as measured by axial slice). When the reconstruction is done with the scatter correction only for inside FOV activity (but without correction for outside FOV activity), the measured activity increases near the (axial) ends of the FOV. This is due to outside radioactivity scattering into the FOV—the scatter is highest at the ends of the FOV and decreases with increasing distance into the FOV (and hence away from the outside-FOV scatter sources). The measured activity is 10% higher (denoted ΔC in FIG. 3B) than that of the reconstruction performed with the scatter correction for the outside FOV activity as disclosed herein. This large value of ΔC illustrates the value of providing a relatively accurate quantitative estimate of the radiopharmaceutical distribution outside FOV scatter correction as disclosed herein; rather than correcting for the scatter from measured activity inside FOV only. Some conventional techniques can be still employed such as approximating the unknown activity distribution in the extended FOV along an axial direction as the same as that measured in the outermost (i.e. peripheral) axial slices of the FOV, however, this assumption never holds in the clinical patient imaging, and may often lead to either overcorrection or undercorrection for scatter.

Figure 4:
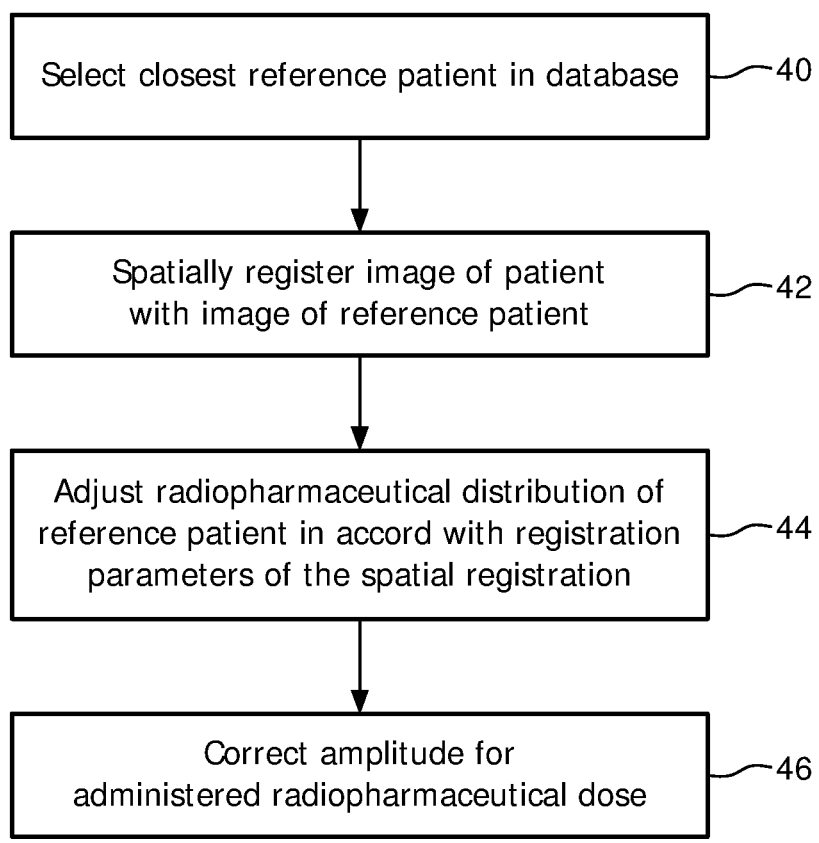
FIG. 4 shows one illustrative method for estimating the radiopharmaceutical distribution in an extended FOV outside of and adjacent the imaging FOV.

With reference to FIG. 4, a method is described that is suitably performed by the processing block 34 to estimate the radiopharmaceutical distribution in the patient based on the patient image collected in the operation 30 and contents of the database 32. The method of FIG. 4 assumes that the operation 30 collects an image of the patient (but does not directly image the radiopharmaceutical distribution). The method further assumes that the database 32 contains, for each of a set of reference patients: (1) an image of the reference patient; and (2) a corresponding radiopharmaceutical distribution in the reference patient. In an operation 40, the reference patient in the database 32 that is closest to the patient currently undergoing PET imaging is selected. This selection may be based on various factors, such as patient characteristics (height, weight, body fat metric, gender, et cetera), radiopharmaceutical type, radiopharmaceutical dosage, time interval between administering the radiopharmaceutical and the PET imaging (since the distribution may depend on how long it has had to diffuse through the body and collect in the target tissue or organ), a medical condition that is expected to impact the radiopharmaceutical distribution, and so forth. In an operation 42, the image of the selected reference patient obtained from the database 32 is spatially registered to the image of the patient acquired in the operation 30. The spatial registration can employ a rigid or non-rigid spatial registration technique, and generally entails stretching, shrinking, or otherwise deforming the reference patient image along with suitable translational and rotational operations in order to align with the image of the current patient obtained in the operation 30. In an operation 44, the corresponding radiopharmaceutical distribution of the reference patient, also obtained from the database 32, is deformed in accordance with the deformation parameters of the spatial registration. For example, the appropriate translational and/or rotational adjustments are applied, and if in the operation 42 the reference patient image was stretched by 10% in the axial (i.e. superior-inferior) direction, by 6% in the posterior-anterior direction, and by 8% in the lateral direction, then these deformational operations are also applied to the radiopharmaceutical distribution of the reference patient. In an operation 46, other adjustments may be applied, such as correcting for the administered radiopharmaceutical dosage. For example, if the current patient was administered a radiopharmaceutical dosage that is 20% higher than that administered to the reference patient (where the dosage of the reference patient is again retrieved from the database 32) then the magnitude of the reference radiopharmaceutical distribution is suitably increased by 20% to account for the dosage difference.

In the example of FIG. 4, it is assumed that the database 32 stores an actual image or map of the radiopharmaceutical distributions in the reference patients. In other embodiments, the database 32 may store something less than a full three-dimensional image or map. For example, the radiopharmaceutical distribution may be stored as a parameterized three-dimensional model of the distribution. In this variant, the method of FIG. 4 is again applied, with the operation 44 being modified to adjusting appropriate spatial parameters of the parameterized three-dimensional distribution model in accord with the deformation parameters of the spatial registering. For example, if the model includes a parameter specifying the axial length distribution model, then this parameter is suitably adjusted based on the axial stretching or shrinking applied to achieve spatial registration in operation 42.

As another variant, the spatial registration operation 42 can be replaced by other operations providing equivalent comparative information. In one such approach, during the scan planning phase the PET imaging session, the radiologist is presented with the PET surview image and is asked to specify the activity object boundaries, for example by moving vertical cursors on a GUI display of the surview image to align the cursors with these boundaries. Alternatively, an automatic contouring algorithm can be used to delineate the boundaries of the activity object. Here the database 42 suitably stores reference patient surviews and the corresponding reference patient/current patient activity object boundaries are compared. If the actual activity object is measured by a PET surview, then the adjustment operation 44 can be performed directly based on the reference patient/current patient object boundary comparison, with operation 42 reduced to determining those boundaries as just described.

In another approach, the technology of healthcare big data can be leveraged. A large pool of previously scanned patients (whose images include regions that are outside-FOV in current patient) can be harvested and machine learning algorithms applied to derive a projected emission distribution for a current patient in the extended FOV regions outside the imaging FOV. Patient- and study-specific information as age, sex, height, weight or body-mass-index, injected radiotracer and scanning mode are optionally used in order to more closely match the current patient with the corresponding subset of reference patient scans.

The various data processing components of FIG. 1 are suitably implemented as a computer or other electronic data processing device programmed to: (i) control the radioemission imaging scanner 12 to acquire radioemission imaging data, (ii) control the additional imaging system (if any) used to perform the extended-FOV imaging data acquisition operation 30, and (iii) perform the disclosed imaging data processing operations in order to generate the reconstructed image with outside-FOV scatter correction as disclosed herein.

It will be further appreciated that the imaging data processing techniques disclosed herein may be embodied by a non-transitory storage medium storing instructions readable and executable by an electronic data processing device to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A radioemission imaging system comprising:
a database; and
an electronic data processing device programmed to perform an imaging method including:
operating a radioemission scanner to acquire tomographic radioemission data of a radiopharmaceutical in a subject in an imaging field of view (FOV);
operating an imaging system to acquire extension imaging data of the subject in an extended FOV disposed outside of and adjacent the imaging FOV along an axial direction;
estimating a distribution of the radiopharmaceutical in the subject in the extended FOV based on the extension imaging data including selecting, from the database, a distribution of the radiopharmaceutical in other subjects; and
reconstructing the tomographic radioemission data to generate a reconstructed image of the subject in the imaging FOV including correcting the reconstructed image for scatter from the extended FOV into the imaging FOV based on the estimated distribution of the radiopharmaceutical in the subject in the extended FOV.

2. The radioemission imaging system of claim 1 wherein:
the operating of an imaging system to acquire extension imaging data comprises operating a transmission computed tomography (CT) scanner or magnetic resonance (MR) scanner or optical imaging device scanner to acquire an image of the subject in the extended FOV; and
the estimating comprises estimating the distribution of the radiopharmaceutical in the subject in the extended FOV based on (i) the acquired image of the subject in the extended FOV and (ii) the selected distributions of the radiopharmaceutical in other subjects from the database.

3. The radioemission imaging system of claim 1 wherein:
the operating of an imaging system to acquire extension imaging data comprises operating the radioemission scanner to acquire two- or three-dimensional radioemission data of the radiopharmaceutical in the subject in the extended FOV; and
the estimating comprises estimating a three-dimensional distribution of the radiopharmaceutical in the subject in the extended FOV based on (i) the acquired two- or three-dimensional radioemission data of the subject in the extended FOV and (ii) three-dimensional distributions of the radiopharmaceutical in other subjects stored in the database.

4. The radioemission imaging system of claim 2 wherein the estimating comprises selecting, from the database, a distribution of the radiopharmaceutical in another subject that most closely matches element (i).

5. The radioemission imaging system of claim 4 wherein the estimating further comprises adjusting the selected distribution of the radiopharmaceutical in another subject based on at least one of:
element (i), and
a characteristic of the subject.

6. The radioemission imaging system of claim 1 wherein:
the operating of an imaging system to acquire extension imaging data comprises operating the radioemission scanner to acquire a whole-body radioemission image of the subject that encompasses the extended FOV wherein the whole-body image is of lower resolution than the reconstructed image; and the estimating comprises estimating the distribution of the radiopharmaceutical in the subject in the extended FOV based on the whole-body radioemission image of the subject.

7. The radioemission imaging system of claim 1 further comprising:

a positron emission tomography (PET) scanner, wherein the radioemission scanner is the PET scanner.

8. The radioemission imaging system of claim 1 wherein the correcting comprises correcting the reconstructed image for the estimated distribution of the radiopharmaceutical in the subject in the extended FOV using single scatter simulation (SSS).

9. A non-transitory storage medium storing instructions readable and executable by an electronic data processing device to perform an imaging method including:

receiving tomographic radioemission data of a radiopharmaceutical in a subject in an imaging field of view (FOV);

receiving extension imaging data of the subject in an extended FOV neighboring the imaging FOV;

estimating a distribution of the radiopharmaceutical in the subject in the extended FOV based on the extension imaging data including selecting, from a database, a distribution of the radiopharmaceutical in other subjects and estimating the distribution of the radiopharmaceutical in the subject based on the distribution of the radiopharmaceutical in other subjects selected from the database; and reconstructing the tomographic radioemission data to generate a reconstructed image of the subject in the imaging FOV;

wherein the reconstructing includes correcting the reconstructed image for scatter from the estimated distribution of the radiopharmaceutical in the subject in the extended FOV.

10. The non-transitory storage medium according to claim 9 wherein the imaging method further includes:

acquiring extension imaging data from a transmission computed tomography (CT) scanner or magnetic resonance (MR) scanner or optical imaging device of an image of the subject in the extended FOV; and wherein the estimating further comprises estimating the distribution of the radiopharmaceutical in the subject in the extended FOV based on (i) the acquired image of the subject in the extended FOV and (ii) of the selected distributions of the radiopharmaceutical in other subjects from the database.

11. The non-transitory storage medium according to claim 9 wherein the imaging method further includes:

acquiring low statistics ultrafast scan radioemission data of the radiopharmaceutical in the subject in the extended FOV; and wherein the estimating further comprises estimating a three-dimensional distribution of the radiopharmaceutical in the subject in the extended FOV based on (i) the acquired low statistics radioemission data of the subject in the extended FOV and (ii) three-dimensional distributions of the radiopharmaceutical in other subjects stored in the database.

12. The radioemission imaging system of claim 10 wherein the estimating further comprises selecting, from the database, a distribution of the radiopharmaceutical in another subject that most closely matches element (i).

13. The radioemission imaging system of claim 12 wherein the estimating further comprises adjusting the selected distribution of the radiopharmaceutical in another subject based on at least one of: element (i), and characteristics of the subject.

14. The non-transitory storage medium according to claim 9 wherein the imaging method further includes:

acquiring a whole-body radioemission image of the subject that encompasses the extended FOV wherein the whole-body image is of lower resolution than the reconstructed image; and wherein the estimating further comprises estimating the distribution of the radiopharmaceutical in the subject in the extended FOV based on the whole-body radioemission image of the subject.

15. An imaging method including:

acquiring tomographic radioemission data of a radiopharmaceutical in a subject in an imaging field of view (FOV);

acquiring extension imaging data of the subject in an extended FOV extending beyond the imaging FOV along an axial direction;

estimating a distribution of the radiopharmaceutical in the subject in the extended FOV based on the extension imaging data including selecting, from a database, a distribution of the radiopharmaceutical in other subjects; and reconstructing the tomographic radioemission data to generate a reconstructed image of the subject in the imaging FOV including correcting the reconstructed image for scatter into the imaging FOV from the estimated distribution of the radiopharmaceutical in the subject in the extended FOV.

16. The method of claim 15 further including:

acquiring extension imaging data from a transmission computed tomography (CT) scanner or magnetic resonance (MR) scanner of an image of the subject in the extended FOV; and wherein the estimating further comprises estimating the distribution of the radiopharmaceutical in the subject in the extended FOV based on (i) the acquired image of the subject in the extended FOV and (ii) of the selected distributions of the radiopharmaceutical in other subjects from the database.

17. The method of claim 15 further including:

acquiring two-dimensional radioemission data of the radiopharmaceutical in the subject in the extended FOV; and wherein the estimating further comprises estimating a three-dimensional distribution of the radiopharmaceutical in the subject in the extended FOV based on (i) the acquired two-dimensional radioemission data of the subject in the extended FOV and (ii) three-dimensional distributions of the radiopharmaceutical in other subjects stored in the database.

18. The method of claim 16 wherein the estimating further comprises selecting, from the database, a distribution of the radiopharmaceutical in another subject that most closely matches element (i).

19. The method of claim 18 wherein the estimating further comprises adjusting the selected distribution of the radiopharmaceutical in another subject based on at least one of: element (i), and a characteristic of the subject.

20. The method of claim 15 further including:
acquiring a whole-body radioemission image of the subject that encompasses the extended FOV wherein the whole-body image is of lower resolution than the reconstructed image; and
wherein the estimating further comprises estimating the distribution of the radiopharmaceutical in the subject in the extended FOV based on the whole-body radioemission image of the subject.

\* \* \* \* \*